United States Patent
Bergman et al.

(10) Patent No.: US 6,230,550 B1
(45) Date of Patent: May 15, 2001

(54) METHOD AND APPARATUS FOR MEASURING THE PROPERTIES OF A COMPOSITION OR A COMPONENT THEREOF USED IN THE PROCESSING OF A PAPER OR BOARD WEB

(75) Inventors: John Bergman; Tapio Järvensivu; Mika Leiritie, all of Turke; Ilkka Roitto, Masku, all of (FI)

(73) Assignee: Valmet-Raisio Oy, Raisio (FI)

( * ) Notice: Subject to any disclaimer, the term of this patent is extended or adjusted under 35 U.S.C. 154(b) by 0 days.

(21) Appl. No.: 09/318,044

(22) Filed: May 25, 1999

(30) Foreign Application Priority Data

May 26, 1998 (FI) .......................................... 981170

(51) Int. Cl.$^7$ .......................... G01N 33/34; D21F 11/00
(52) U.S. Cl. ........................................ 73/53.03; 162/198
(58) Field of Search .................................. 73/53.03, 19.1; 162/198, 252, 258

(56) References Cited

U.S. PATENT DOCUMENTS

| | | |
|---|---|---|
| 3,668,566 | 6/1972 | Higgs . |
| 4,151,744 | 5/1979 | Hemmings . |
| 4,584,866 | 4/1986 | Wladmir ............................. 73/19.1 |
| 4,893,496 | 1/1990 | Bau et al. . |
| 5,076,890 | 12/1991 | Balembois . |
| 5,165,292 | 11/1992 | Prohaska . |
| 5,670,709 | 9/1997 | Gallagher . |
| 5,954,922 | 9/1999 | Ramarao ............................. 162/198 |

FOREIGN PATENT DOCUMENTS

| | | |
|---|---|---|
| 2 259 368 | 3/1993 | (GB) . |
| WO 97/24596 | 7/1997 | (WO) . |

OTHER PUBLICATIONS

Martti Mäkinen, Metering Density, Dry Solids and Air Content of Coating in Supply System, 1996 International Paper and Coating Chemistry Symposium, Ottawa, 11.–13 . . 1996.

R. Rauch, R. Sangl, H.–H. Hofer and J. Weigl: Gase in Streichfarben—Auswirkungen auf Lauf– und Qualität-seigenschaften, PTS Streicherei Symposium 97.

I. Roitto, T. Järvensuu and J. Koskinen: The Significance of Deaeration in the Coating Process, PTO Streicherei Symposium.

*Primary Examiner*—Hezron Williams
*Assistant Examiner*—Jay L. Politzer
(74) *Attorney, Agent, or Firm*—Cohen, Pontani, Lieberman & Pavane

(57) ABSTRACT

The present invention relates to a method and apparatus for measuring the properties of a composition or a component thereof used in the processing of a paper or board web. According to the invention, a sample of the composition to be measured is taken into a measurement apparatus, the composition is measured at least for its density, viscosity, dry solids content and gas content, and is then passed out from the measurement apparatus. The apparatus according to the invention comprises an apparatus frame (23), a composition sample conduit (6) adapted in said apparatus frame (23) for passing a flow of said composition under measurement through the apparatus, a pump (7) adapted in said composition sample conduit (6) for circulating said composition through said composition sample conduit (6), means (10, 11, 12, 13, 14, 15, 16, 17) adapted in said composition sample conduit (6) for measuring the density values of said composition as well as the pressure and temperature values of said composition prevailing in the composition at said instant of density measurement, and means (14, 15, 18, 19, 20) adapted in said composition sample conduit (6) for determining the viscosity of said composition.

15 Claims, 1 Drawing Sheet

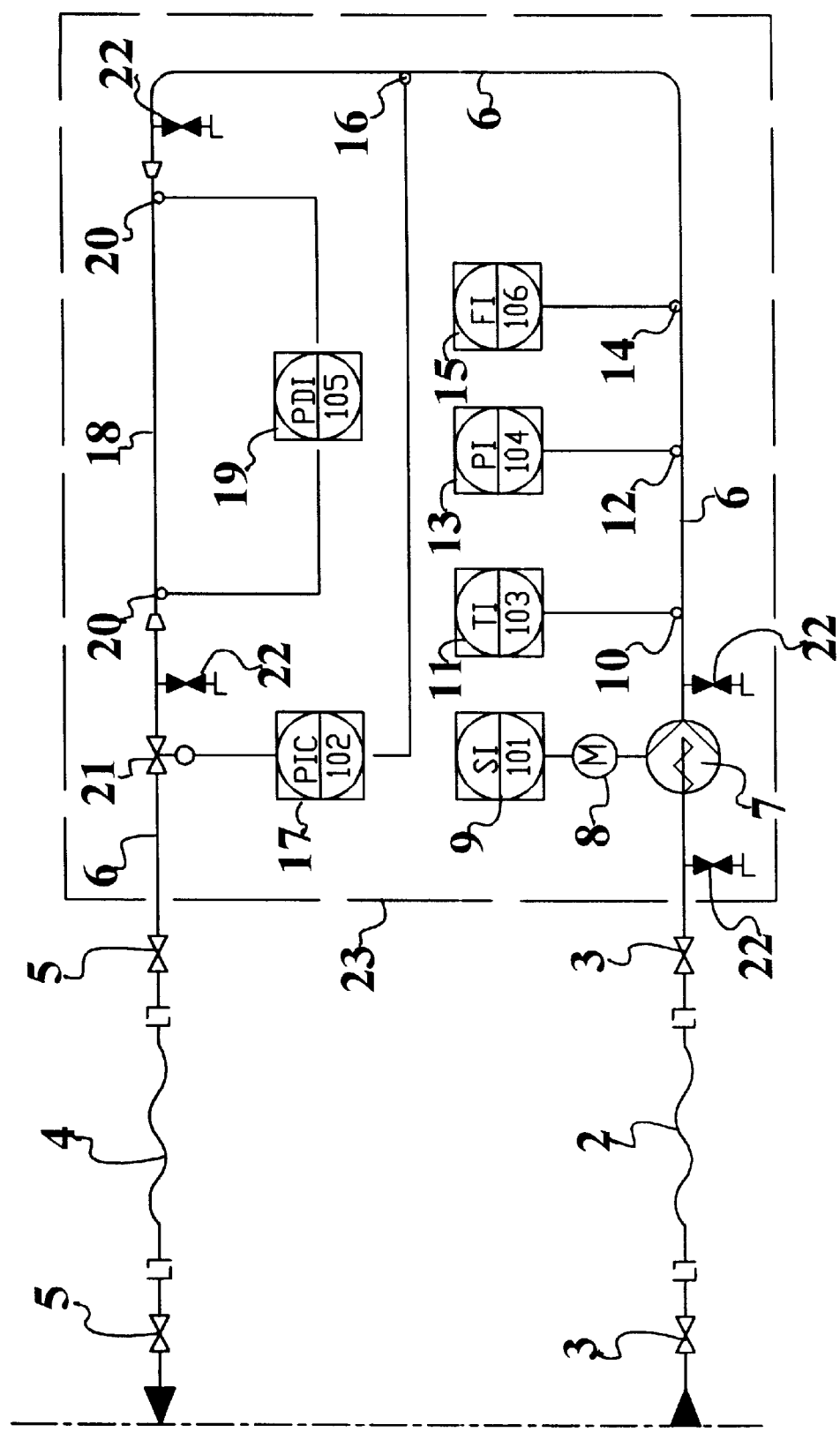

METHOD AND APPARATUS FOR MEASURING THE PROPERTIES OF A COMPOSITION OR A COMPONENT THEREOF USED IN THE PROCESSING OF A PAPER OR BOARD WEB

FIELD OF THE INVENTION

The invention relates to a method and apparatus for determining the properties of compositions and components thereof used in the processing of a paper and board web. Such compositions are, e.g., filler compositions, coating compositions in the form of pastes and pigment slurries and concentrated pigment slurries for use in the preparation of a coating mix. The properties to be determined from the compound under measurement are, e.g., temperature, density, solids content (SC), content of free gases, content of dissolved gases, viscosity, shear stress and yield point. Also other qualities related to the rheology of the compound may be subject to measurement.

BACKGROUND OF THE INVENTION

Properties of primary importance in a coating mix are its viscosity, solids content and gas content. Generally, the gas content is known as the air content, because the gas entrained in the coating mix is chiefly air. The information obtained from the measurements can be utilized, e.g., in the control of a coating process or preparation of a coating mix. Herein, the parameters to be controlled are, e.g., the amount of diluting solution to be added to the coating mix, the composition of the coating mix or the efficiency of the air purging apparatus used.

The properties of the coating mix are reflected in the quality of the final coat. For instance, the viscosity of the coating mix has an influence over the entire coating process. As the viscosity of the coating mix governs the flow properties of the coating in the interior of the applicator apparatus, obviously the operation of the coater itself is affected thereby. The coating mix viscosity also contributes to the thickness and final quality of the applied coat. Even relatively small changes in the coating mix composition can be seen in the coating mix viscosity and, thus, in the final coat quality. The coating mix viscosity in turn can be controlled by altering the mutual proportions and selection of the components used in the coating mix formula.

Also the gas content of the applied coating mix affects the attainable coat quality. An excessively high gas content gives rise to quality degradation, in addition to causing foaming in the coating mix containers. To avoid such problems, the machine circulations of coaters are generally complemented with such aids as centrifugal air purging units or, alternatively, the use of antifoam chemicals. For effective control of gas purging, the system should be equipped with a gas content analyzer.

In the prior art, the properties of a coating mix have been determined by first sampling the coating mix to be applied and then analyzing the samples in a laboratory. This approach is handicapped by involving such a long delay between the sampling instant and the assessment of the laboratory results that the online properties of the coating mix have already changed during the delay. When taking samples from the machine circulation of a coater station, a further difficulty has been experienced from the release of the entrained gas from the sample to the surroundings prior to the measurement of the sample. In other respects, too, this type of so-called off-line technique has not been found practical in the attempt to reduce the short-term variations of coating mix properties. Off-line measurement methods and the characteristics of coating formulas are described, e.g., in a publication authored by I. Roitto, T. Jarvensuu and J. Koskinen: "The Significance of Deaeration in the Coating Process", PTS Streicherei Symposium 97.

This publication also suggests that the density of a coating mix can be measured by an on-line type of measurement using a mass flow rate measurement instrument. If such a measurement is carried out at two different pressures selected in a suitable manner, the gas content of the coating mix can also be determined.

Furthermore, in a publication by R. Rauch, R. Sangl, H.-H. Hofer and J. Weigl: "Gase in Streichfarben—Auswirkungen auf Lauf—und Qualitätseigenschaften", PTS Streicherei Symposium 97, is described an on-line method for measuring the gas content of a coating mix. This method is based on passing a sample of the coating mix from the machine circulation of the coater via a piping into a measurement chamber having temperature and pressure sensors adapted therein. The measurement chamber is also provided with a stepper motor and a piston suited for adjusting the interior volume of the measurement chamber. As an additional feature, the interior volume of the chamber can be determined from the position of the stepper motor. After the pressure and temperature of the coating mix are measured using at least two different volumes of the measurement chamber, the gas content of the coating mix can be computed from known physical formulas. After the measurement, the measured sample can be returned back to the machine circulation and the measurement chamber can be flushed.

Also the on-line measurement of coating mix viscosity is known in the art. A plurality of different techniques for measuring viscosity have been disclosed in the prior art. In regard to a coating mix, a particularly advantageous technique of viscosity measurement is the capillary measurement method. This method is based on passing the coating mix flow via a capillary tube and then computing the viscosity from the pressure loss across the capillary tube that can be measured with the help of a differential pressure transducer, for instance.

A drawback of conventional techniques is that, for a multivariable assessment of coating mix properties, a plurality of separate measurement equipment must be connected to the machine circulation. This is a clumsy arrangement in which the measurement data and accuracy of results are difficult to control. Such a system may also require the same parameters to be measured several times in conjunction with the separate measurements. A further problem in the use of separate measurement apparatuses is that the composition of the coating mix under measurement may change from one measurement point to another. Finally, it must be noted that an on-line method for the measurement of dry solids content in a coating mix has not been disclosed in the prior art.

SUMMARY OF THE INVENTION

It is an object of the invention to overcome the above-described problems and to provide an entirely novel type of method and apparatus for measuring the properties of a coating mix.

The goal of the invention is achieved by means of routing a portion of the coating mix to be measured aside from the machine circulation of a coater, a coating mix preparation system or similar equipment so as to obtain a continuous bypass sample flow or a sequence of discrete samples. The bypass sample flow or the discrete samples are taken into a piping and therefrom to measurement apparatuses capable of measuring the variables required for the determination of at least the density, viscosity, dry solids content and gas content of the coating mix. According to the invention, at least the viscosity and solids content of the coating mix are determined based on the measured variables. Further according to the invention, the required measurement devices are connected to a common control unit.

The invention provides significant benefits.

The invention makes it possible to determine the viscosity, dry solids content and gas content of a composition using an integrated system which is connected to the machine circulation of the composition by a single set of inlet/outlet connections.

A preferred embodiment of the invention is characterized by a further feature of allowing the number of measurement sensors to be reduced over those required in conventional measurement techniques based on the use of separate measurement devices. This is because the common control system facilitates the utilization of previously measured coating mix parameters in the determination of values for certain other variables, whereby the need for measuring, e.g., pressure and temperature separately in each measurement device, is eliminated. Thus, the invention offers a cost-effective solution to attain a higher measurement accuracy.

When the invention is implemented using a capillary-tube-based viscosity measurement, a preferred embodiment of the invention offers a further benefit that the pressure measurement values required for the determination of some variables can be utilized for setting the measurement span of the differential pressure transmitter of the viscometer to a proper range. This arrangement gives an essential improvement in the measurement accuracy.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

In the following the invention will be examined in greater detail with reference to examples and the appended FIGURE.

The FIGURE shows a flow diagram of an apparatus according to the invention.

DETAILED DESCRIPTION OF THE PRESENTLY PREFERRED EMBODIMENTS

In the embodiment illustrated in the FIGURE, the measurement apparatus is connected to a paper or board coater in which the web treatment composition is a coating mix. However, the apparatus and method described in the exemplifying embodiment may as well be applied to the measurement of other compositions with similar properties such as pigment slurries.

In FIGURE is shown a main pipe 1 of the machine circulation along which a coating mix or pigment slurry is passed to the applicator units of the coater. To the pipe 1 is connected a sample inlet conduit 2 for taking a coating mix sample into the measurement apparatus. The sample inlet conduit 2 is provided with valves 3 with which the coating mix sample flow into the measurement apparatus can be cut off when desired. To the pipe 1 is also connected a sample outlet conduit 4 along which the coating mix sample can be passed back into the pipe 1. Respectively, the sample outlet conduit 4 is provided with valves 5 with which the outlet conduit can be cut off when desired.

The actual measurement apparatus comprises a sample conduit 6 along which the sequence of coating mix samples or the continuous bypass sample flow entering from the sample inlet conduit 2 is passed through the measurement apparatus to the sample outlet conduit 4. To the sample conduit 6 is placed a pump 7 driven by a variable-speed electric motor 8. The electric motor 8 in turn is controlled by driver/controller means 9. In the sample conduit 6, next after the pump 7, is placed a temperature sensor 10 serving to measure the temperature of the coating mix sample. The temperature sensor 10 is connected to a temperature transmitter 11. Next after the temperature sensor 10, the sample conduit 6 is provided with a first pressure sensor 12 with a pressure transmitter 13 connected thereto serving to measure the pressure of the sample at the pressure sensor 12.

Next in the sample conduit 6 is placed a density transmitter and a mass or volumetric flow rate transmitter that in the diagram are illustrated as an integrated instrument. Herein, the apparatus has a transducer bead 14 and a measurement unit 15 for density and mass or volumetric flow rate measurement. Next along the sample conduit 6, after the transducer head 14, is placed a second pressure transducer 16 suited for measuring the pressure prevailing in the coating mix sample after the combination density and flow rate transmitter. The second pressure transmitter 16 is connected to a measurement/control device 17. After the pressure transmitter 16, the conduit 6 is provided with a viscometer. In the diagram, the viscosity measurement is shown implemented using the capillary method in which the viscometer comprises a capillary tube 18, a differential pressure transmitter 19 and measurement nozzles 20 placed close to the first and second ends of the capillary tube 18 for providing measurement signals to a differential pressure transmitter 19 on the internal pressures of the coating mix at the respective first and second ends of the capillary tube 18. Next after the viscometer, the sample conduit 6 is further provided with a control valve 21 suited for adjusting the flow resistance of the coating mix and thereby, the internal pressure in the sample conduit 6. The control valve 21 is steered by a measurement/control device 17 that monitors the pressure of the sample conduit 6 by means of the pressure sensor 16. Other components shown in the diagram are drain valves 22 connected to the sample conduit 22 and the apparatus frame 23 proper.

The measurement apparatus also includes a control and computing system not shown in the diagram. The control and computing system is connected, e.g., by cables at least to the electric supply and control means 9 of the electric motor 8, the temperature transmitter 11, the pressure transmitter 13, a combination measurement unit 15 for density and mass or volumetric flow rate, the measurement/control device 17 and the differential pressure transmitter 19. The function of the control and computing system is to steer the above-listed instruments and/or gather information therefrom and, based thereon, to compute the desired properties of the coating mix under measurement. The implementation of these functions is described in greater detail later in the text. One further function of the control and computing system is to provide a communications facility between the measurement apparatus and its operating environment. For this purpose, the control and computing system can be complemented, e.g, with, a keyboard, switches, display and/or a computer interface.

The pipe 1, from which the discrete samples or a continuous sample flow are/is taken, may in principle be any pipe or container filled with a material suitable for being measured. To measure the properties of a coating mix used for application to a paper or board sheet, the sample inlet conduit 2 is advantageously connected after the air-purging unit to the main feed line passing the coating mix to the coater. Thence it is also possible to measure accurately the final value of the coating mix air content prior to application. Also the outlet conduit 4 is advantageously connected to the main feed pipe 1, whereby the coating mix passed through the measurement apparatus can be recovered for use in coating. Advantageously, the sample outlet conduit 4 is connected to the flow of the feed pipe 1 after the connection of the sample inlet conduit 2. The sample inlet conduit 2 and the sample outlet conduit 4 themselves can be made, e.g., from a high-pressure hose. The sample conduit 6 itself can be made, e.g., from a metal pipe with an inner diameter of about 5–25 mm.

The pump 7, the electric motor 8 and the electric supply and control means 9 thereof must be selected such that the flow rate and pressure of the coating mix can be set to proper values for each measurement situation by adjusting the speed of the pump 7. The pressure setting can also be performed by virtue of adjusting the flow resistance with the help of the control valve 21. For measuring the air content of the coating mix, the internal pressure of the sample conduit at the transducer head 14 of the density measurement unit 15 must be arranged to be alternatingly adjustable between a sufficiently low and a sufficiently high value. The lower pressure used for measuring the density of coating mix containing air bubbles can be set, e.g., to about 0.5–3 bar. The higher pressure must respectively be set sufficiently high to cause an essential dissolution and compression of the air contained in the coating mix so that the air-free density of the coating mix can be measured. The required pressure is dependent on the capability of the coating mix to dissolve air or other gas contained in the composition as well as on the amount of air or gas entrained in the mix. A more detailed description of the effect of air bubbles on the measurement is given in a paper by M. Mäkinen, "Metering Density, Dry Solids and Air Content of Coating in Supply Systems", 1996 International Paper and Coating Chemistry Symposium, Ottawa, 11.0–13.6.1996. As a guideline it can be mentioned the upper pressure may be about 10–30 bar and preferably never smaller than 6 bar. Typically, the sample flow rates of coating mix used in the measurement are in the range 0–20 l/min. Other typical guideline values characterizing the sample flow at the viscometer are, e.g., a coating mix shear rate of 1–10,000 1/s, Reynold's number in the range 0–3000 and Dean's number in the range 0–30.

The temperature sensor 10 and the temperature transmitter 11 are selected so that the temperature of the coating mix sample can be measured with a sufficient accuracy. The required measurement span must cover the typical temperature range of a coating mix, that is, about 10–80° C. typical. The sample temperature is required in the calculations of dry solids in order to determine the actual value of water density and, in some cases, also the actual solids density, in the sample during its density measurement.

Respectively, the first and the second pressure sensor 12, 16 as well as the pressure transmitter 13 and the measurement/control device 17 connected thereto must be suitable for measuring the internal pressure of the coating mix sample. The measured pressure values are used for determining the internal pressure prevailing in the coating mix sample contained in the density transmitter. In turn, the internal pressure of the density transmitter is used for computing the air or gas content of the coating mix sample. Obviously, the thus obtained pressure value is also utilized in the control of the pump 7 and the control valve 21. The operating pressure span required from the pressure sensors 12, 16 is typically 0.1–30 bar.

The density transmitter and the mass or volumetric flow transmitter can be implemented as separate instruments using any type of conventional device. Alternatively, a combination instrument may be used capable of measuring both of the desired variables. The density measurement can be performed, e.g., using a method based on the measurement of hydrostatic pressure at two different heights from a column of coating mix placed in a vertical tube. Furthermore, density measurement can be carried out by methods based on the use of microwave or radioactive radiation. The measurement of volumetric flow rate can be performed, e.g., using a magnetic flow rate meter. A particularly advantageous measurement technique is the Coriolis effect mass flow measurement that is capable of combining both the mass flow rate and the density measurement. In an instrument based on the Coriolis effect, the measurement head 14 comprises at least one tubular flow conduit and means suited to make each flow tube to vibrate at its resonant frequency. The measurement head also includes detectors adapted to measure the deflection of the flow tube. During the measurement, the material to be measured is passed through the flow tube, whereby the material contained in the tube imposes forces resisting the vibration of the tube. These forces deflect the flow tube or tubes, whose deflection can be measured with the help of the detectors. The detector signal indicating the deflection is taken to a measurement unit 15 of the Coriolis effect flow meter, wherein the mass flow rate corresponding to the amplitude of the deflection is computed. Respectively, the density of the material contained in the flow tube can be determined with a good accuracy from the resonant frequency of the vibrating flow tube filled with the material and from the internal volume of the vibrating flow tube. This measurement technique is based on the fact that the mass of the material filling the flow tube affects the resonant frequency of the flow tube. The densities of coating mixes to be measured typically vary in the range 900–2000 kg/m$^3$ and the mass flow meter may operate using mass flow rates in the order of 0–5 kg/s, for instance.

The density measurements for the coating mix to be measured for gas content calculation in conjunction with a Coriolis effect mass flow meter are carried out, e.g., in the following manner:

Coating mix is passed via the flow tube of the measurement head 14 by means of driving the pump 7 at such a speed and by steering the control valve 21 into such a position that the coating mix pressure in the flow tube will be about 2–3 bar. The internal pressure in the flow tube is determined from the pressure signals of the first and second pressure transducers 12, 16 as their mean value, for instance. When required, also an appropriate calibration factor can be applied. In this manner, the pressure loss of the flow tube that may be in the range 0.1–2 bar will be compensated for. The measurement value thus obtained is density p, at internal pressure $P_1$.

Next, the pump 7 and the control valve 21 are first steered so that the internal pressure in the flow tube rises to about 6–10 bar, and then density $\rho_2$ is measured at internal pressure $P_2$. If there is a reason to assume that the volume of gas bubbles in the coating mix cannot be neglected, a higher pressure must be used.

The gas content $I_1$ of the coating mix is computed at said lower pressure $P_1$ utilizing the assumption that the volume of contained gas bubbles at the higher pressure $P_2$ has been negligible. Now, the gas content $I_1$ is computed from the formula:

$$I_1 = \left(1 - \frac{\rho_1}{\rho_2}\right) \times 100\ \%. \qquad (1)$$

Herefrom, the gas content $I_1$ of the measured coating mix sample at atmospheric pressure $P_1$ can be computed from the formula:

$$I_i = \frac{P_2}{P_i} \times I_1. \qquad (2)$$

In turn, the solids content SC can be determined from the dry solids density $\rho_{dry}$ of the coating mix with the help of the essentially gas-bubble-free density $\rho_2$ of the mix measured at the higher pressure and from the density $\rho_{water}$ of water using the formula:

$$SC = \frac{\rho_{dry}(\rho_2 - \rho_{water})}{\rho_2(\rho_{dry} - \rho_{water})}. \qquad (3)$$

When determining the density values required in Eq. 3, care must be taken to assure that the values $\rho_{dry}$, $\rho_2$ and $\rho_{water}$ applied to the formula are sufficiently accurate to represent the actual densities at the same temperature. The densities can be determined in the following manner, for instance:

The coating mix density $\rho_2$ is measured and simultaneously is recorded the temperature reading $T_{SC}$ obtained at the measurement instant from the temperature transmitter 11.

Water density $\rho_{water}$ at the recorded coating mix temperature $T_{SC}$ is obtained from, e.g., a table or formula stored in the control and computing system.

The dry solids density $\rho_{dry}$ is determined, e.g., by computing from the component densities of the composition. This computation need not necessarily be done in the measurement apparatus, but rather, $\rho_{dry}$ is typically computed in a separate system and then entered therefrom into the measurement apparatus. If the temperature coefficient of expansion of the dry solids is very small, the measurement temperature of density value $\rho_2$ can be neglected in the determination of the dry solids density $\rho_{dry}$.

Viscosity can be measured in a plurality of different techniques. In the prior art, the viscosity of coating mixes has been measured using, e.g., methods based on the motion or flow resistance of suitably shaped bodies in the flow of the coating mix. Viscosity can also be measured by passing the coating mix into a suitably shaped conduit and then measuring the pressure drop of the coating mix flowing through the conduit. One such method particularly well suited for measuring the viscosity of coating mix is the so-called capillary tube method. In this method the coating mix is passed through the bore of a straight capillary tube 18 of constant cross section and the pressure drop is measured at measurement points 20 placed at a distance from each other in the capillary tube 18. The capillary tube method is especially preferred for the viscosity measurement of coating mixes and component thereof, because by being based on apparatus constants only, this method disposes with the need for any material-specific calibration coefficients. Such calibration coefficients would cause substantial uncertainty in the measurement, since coating mixes, for instance, typically are non-Newtonian fluids.

The sample viscosity can be determined from the measurement results in the following manner:

The shear rate $\gamma$ is computed from the formula:

$$\gamma = \frac{4 \times \dot{V}}{\pi \times r^3}\ [1/s], \qquad (4)$$

where $\dot{V}$ is the volume rate of the coating mix being passed into the capillary tube 18 and r is the bore radius of the capillary tube 18. If the flow rate $\dot{V}$ is not measured directly, it can be computed by dividing the measured mass flow rate by the measured density.

The shear stress r is computed from the formula:

$$\tau = \frac{r \times \Delta p}{2 \times \Delta L}\ [\text{Pa}], \qquad (5)$$

where $\Delta p$ is the differential pressure measured across the measurement points of the capillary tube 18 and $\Delta L$ is the distance between the measurement points of the differential pressure.

The viscosity $\eta$ is computed from the formula:

$$\eta = \frac{\tau}{\gamma}\ [\text{Pa s}]. \qquad (6)$$

Thus, an advantageous viscometer construction comprises a capillary tube 18, a differential pressure transmitter 19 and measurement nozzles 20 connected to the capillary tube 18, close to its first and second ends. The length of the capillary tube used herein can be, e.g., from 30 cm to 10 m and the bore cross section of the flow conduit may be in the range of about 5–25 mm. Typically, the pressure drop across this kind of capillary tube 18 can be, e.g., from 0.01 bar to 4 bar. However, the absolute pressure in the capillary tube 18 may be substantially higher. A proper measurement span for the differential pressure transmitter 19 can be, e.g., 0–30 bar. As the measurement resolution of a differential pressure transmitter is generally dictated by the width of the measurement span used therein, the measurement span is advantageously made as narrow as possible. On the other hand, difficulties will be encountered in the limitation of the measurement span because of the wide variations of pressure differences occurring in the measurements.

Herein, the measurement accuracy of a differential pressure transmitter can be improved essentially by utilizing in the measurement span control of the differential pressure transmitter 19 the information available from the pressure transmitter 13 and the measurement/control device 17 on the pressure drop across the measurement head 14 of the combination measurement unit 15 of density and mass/volumetric flow rate. After determining the relationship between the pressure drops across the measurement head 14 and the capillary tube 18, the measurement span of the differential pressure transmitter 19 can be set so as to substantially cover the estimated range that is computed from the differential pressure measured across the measurement head 14. The correspondence between the differential pressures across the measurement head 14 and the capillary tube 18 can be determined, e.g., by experimental means individually for each apparatus construction. Alternatively, a suitable theoretical model can be applied or, furthermore, the sample conduit 6 can be provided with an additional pressure transducer placed in the flow direction after the capillary tube 18, whereby the comparison of this pressure transducer reading with that of the pressure transmitter 16 gives an estimate for the actual differential pressure across the capillary tube 18. This kind of arrangement makes it possible to limit the measurement span required from the differential pressure transmitter 19 so as to match the span with the actually required range of pressure difference. In the above-described manner, the accuracy of viscosity measurement can be improved up to ten-fold over conventional techniques.

The arrangement of measurement means illustrated in the diagram is advantageous for the above-described selection of measurement devices. The proposed order having the combination density-mass flow rate transmitter placed in front of the capillary tube viscometer has the benefit that a higher measurement pressure can be produced from the density measurement with a smaller pump output pressure. Simultaneously, the pressure in the capillary tube remains lower. However, this order and type of measurement means is not limiting to the application of the invention, but rather, a different order of measurement instruments can also be used in an apparatus according to the invention. Particularly when a different type of measurement technique is utilized for obtaining the value of some variable, a different arrangement of the measurement means may be pertinent. Obviously, the apparatus construction can be complemented with additional instruments for measuring some additional parameters.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or methods steps which perform substantially the same function in substantially the same way to achieve the same results are within the scope of the invention. Substitutions of elements from one described embodiment to another are also fully intended and contemplated. It is also to be understood that the drawing is not necessarily drawn to scale but that it is merely conceptual in nature. It is the intention, therefore, to be limited only as indicated by the scope of the claims appended hereto.

What is claimed is:

1. A method of measuring physical properties of a composition or a component thereof used in the processing of a paper or board web, the method comprising the steps of:
   diverting a sample of the composition to be measured from a continuous flow of the composition to a measurement apparatus;
   lacing the sample at a first pressure level, the first pressure level being such that a substantial portion of the gas contained in the composition is in the form gas bubbles;
   measuring a first density value of the composition at the first pressure level;
   changing the pressure level of the composition to a second pressure level, the second pressure level being such that a substantial portion of the gas contained in the composition is at least one of dissolved in the composition and in an essentially compresses gaseous form;
   measuring a second density value of the composition at the second pressure level;
   measuring a temperature of the composition;
   measuring a viscosity of the composition;
   determining a dry solids density of the composition;
   determining a density of water at the measured temperature of the composition;
   computing a dry solids content of the composition from the measured and determined values; and
   discharging the sample from the measuring apparatus after said measuring and determining steps to the continuous flow of the composition.

2. The method of claim 1, wherein the composition is coating mix and the sample is removed from a machine circulation of a coater from the immediate vicinity of a coating applicator of the coater.

3. The method of claim 2, wherein after said measuring and determining steps the sample is discharged into the machine circulation of the coater.

4. The method of claim 1, wherein the composition is a pigment slurry used in preparing a coating mix and the sample is removed from preparation equipment of the slurry.

5. The method of claim 1, wherein the density and the pressure in the composition are determined while said steps of determining density values of the composition is determined, comprising the following steps in sequence:
   passing the composition into a Coriolis-type mass flow meter in which the density of the composition is measured;
   measuring an inlet pressure of the composition entering the Coriolis-type mass flow meter;
   measuring an outlet pressure of the composition leaving the Coriolis-type mass flow meter; and
   determining from the inlet pressure and the outlet pressure a pressure prevailing in the composition while the density of the composition is measured.

6. The method of claim 1, further comprising determining gas content of the composition from the first density value of the composition at the first pressure level, the second density value of the composition at the second pressure level, a value of the first pressure level, and a value of the second pressure level.

7. The method of claim 1, wherein the viscosity of the composition is measured by the following steps in sequence:
   passing the composition into a capillary tube;
   determining a volumetric flow rate of the composition into the capillary tube;
   measuring a differential pressure of the composition at two measurement points in the capillary tube spaced a distance from one another; and
   computing the viscosity from the volumetric flow rate, the measured differential pressure, and dimensions of the capillary tube.

8. An apparatus for measuring physical properties of a composition or a component thereof used in the processing of a paper or board web, comprising:
   a frame;
   a composition sample conduit mounted to said frame for passing a sample of the composition from a continuous flow of the composition;
   a means for setting a pressure of the composition passing through said composition sample conduit;
   a means for measuring a pressure of the composition passing through said composition sample conduit;
   a means for measuring a temperature of the composition passing through said composition sample conduit;

a pump operatively positioned to circulate the composition through said composition sample conduit;

a control valve at an outlet end of said composition sample conduit for setting, in cooperation with said pump, the pressure of the composition being passed through said composition sample conduit to a desired pressure value;

a means for measuring a density of the composition passing through said composition sample conduit;

a means for measuring a viscosity of the composition passing through said composition sample conduit;

a means for obtaining a dry solids density of the composition passing through said composition sample conduit;

a means for obtaining a density of water at a temperature measured by said temperature measuring means of the composition passing through said composition sample conduit; and a means for computing a dry solids content of the composition passing through said composition sample conduit.

9. The apparatus of claim 8, wherein said means for measuring a temperature of the composition comprises a temperature transmitter, said means for measuring a pressure of the composition comprises a first and a second pressure transmitter, and said means for measuring a density of the composition comprises a density transmitter and one of a mass and a volumetric flow rate transmitter.

10. The apparatus of claim 9, wherein said first pressure transmitter is positioned upstream of said density transmitter, and said second pressure transmitter is positioned downstream of said density transmitter.

11. The apparatus of claim 9, wherein said density and one of a mass and a volumetric flow rate transmitter being comprised of a single, Coriolis-type mass flow meter.

12. The apparatus of claim 10, wherein said density and one of a mass and a volumetric flow rate transmitter being comprised of a single, Coriolis-type mass flow meter.

13. The apparatus of claim 8, wherein said means for measuring a viscosity of the composition comprises a capillary tube, a differential pressure transmitter, and at least two measurement nozzles to measure internal pressure of the capillary tube at two measurement points in the capillary tube spaced a distance from one another, the measured internal pressure at the two points being transmitted to said differential pressure transmitter.

14. The apparatus of claim 12, wherein said means for measuring a viscosity of the composition comprises a capillary tube, a differential pressure transmitter, and at least two measurement nozzles to measure internal pressure of the capillary tube at two measurement points in the capillary tube spaced a distance from one another, the measured internal pressure at the two points being transmitted to said differential pressure transmitter.

15. The apparatus of claim 14, wherein said capillary tube is downstream of said first pressure transmitter, said Coriolis-type mass flow meter and said second pressure transmitter.

* * * * *